US012762401B2

(12) United States Patent
Gubbi Lakshminarasimha et al.

(10) Patent No.: US 12,762,401 B2
(45) Date of Patent: Oct. 13, 2026

(54) METHOD AND SYSTEM FOR EEG MOTOR IMAGERY CLASSIFICATION

(71) Applicant: Tata Consultancy Services Limited, Mumbai (IN)

(72) Inventors: Jayavardhana Rama Gubbi Lakshminarasimha, Bangalore (IN); Adarsh Anand, Bangalore (IN); Kartik Muralidharan, Bangalore (IN); Arpan Pal, Kolkata (IN); Vivek Bangalore Sampathkumar, Bangalore (IN); Ramesh Kumar Ramakrishnan, Bangalore (IN)

(73) Assignee: Tata Consultancy Services Limited, Mumbai (IN)

( * ) Notice: Subject to any disclaimer, the term of this patent is extended or adjusted under 35 U.S.C. 154(b) by 675 days.

(21) Appl. No.: 18/334,718

(22) Filed: Jun. 14, 2023

(65) Prior Publication Data

US 2024/0104377 A1 Mar. 28, 2024

(30) Foreign Application Priority Data

Sep. 19, 2022 (IN) ............................ 202221053592

(51) Int. Cl.
*G06N 3/08* (2023.01)
*A61B 5/00* (2006.01)
(Continued)

(52) U.S. Cl.
CPC ............... *G06N 3/08* (2013.01); *A61B 5/369* (2021.01); *A61B 5/7221* (2013.01); *A61B 5/374* (2021.01); *A61B 5/7267* (2013.01); *G16H 50/20* (2018.01)

(58) Field of Classification Search
CPC ........ G06N 3/08; A61B 5/369; A61B 5/7221; A61B 5/374; A61B 5/7267; G16H 50/20
See application file for complete search history.

(56) References Cited

PUBLICATIONS

Jiang X, Ji P. Li S. CensNet: Convolution with Edge-Node Switching in Graph Neural Networks. Inljcai Aug. 10, 2019 (pp. 2656-2662). (Year: 2019).*

(Continued)

*Primary Examiner* — Michelle T Bechtold
*Assistant Examiner* — Nicholas S Wu
(74) *Attorney, Agent, or Firm* — Finnegan, Henderson, Farabow, Garrett & Dunner LLP

(57) ABSTRACT

This disclosure relates generally to the field of Electroencephalogram (EEG) classification, and, more particularly, to method and system for EEG motor imagery classification. Existing deep learning works employ the sensor-space for EEG graph representations wherein the channels of the EEG are considered as nodes and connection between the nodes are either predefined or are based on certain heuristics. However, these representations are ineffective and fail to accurately capture the underlying brain's functional networks. Embodiments of present disclosure provide a method of training a weighted adjacency matrix and a Graph Neural Network (GNN) to accurately represent the EEG signals. The method also trains a graph, a node, and an edge classifier to perform graph classification (i.e. motor imagery classification), node and edge classification. Thus, representations generated by the GNN can be additionally used for node and edge classification unlike state of the art methods.

12 Claims, 4 Drawing Sheets

(51) Int. Cl.
*A61B 5/369* (2021.01)
*A61B 5/374* (2021.01)
*G16H 50/20* (2018.01)

(56) References Cited

PUBLICATIONS

Gong, Ting, et al. "A comparison of loss weighting strategies for multi task learning in deep neural networks." IEEE Access 7 (2019): 141627-141632. (Year: 2019).*
Demir A, Koike-Akino T, Wang Y, Erdogmus D, Haruna M. EEG-GNN: Graph Neural Networks for Classification of Electroencephalogram (EEG) Signals. (Year: 2021).*
Li Y, Zhong N, Taniar D, Zhang H. Mutualgraphnet: a novel model for motor imagery classification. arXiv preprint arXiv:2109.04361. Sep. 2, 2021. (Year: 2021).*
Cai S, Li H, Wu Q, Liu J, Zhang Y. Motor imagery decoding in the presence of distraction using graph sequence neural networks. IEEE Transactions on Neural Systems and Rehabilitation Engineering. Jun. 14, 2022;30:1716-26. (Year: 2022).*
Andac Demir et al., "EEG-GAT: Graph Attention Networks for Classification of Electroencephalogram (EEG) Signals," 2022 44th Annual International Conference of the IEEE Engineering in Medicine & Biology Society (EMBC), Apr. 2022, IEEE, https://www.merl.com/publications/docs/TR2022-097.pdf.
Andac Demir et al. "EEG-GNN: Graph Neural Networks for Classification of Electroencephalogram (EEG) Signals," 2021 43rd Annual International Conference of the IEEE Engineering in Medicine & Biology Society (EMBC), Nov. 2021, IEEE, https://arxiv.org/pdf/2106.09135.pdf.
Biao Sun et al., "Adaptive Spatiotemporal Graph Convolutional Networks for Motor Imagery Classification," IEEE Signal Processing Letters, Jan. 2021, vol. 28, pp. 219-223, IEEE, https://ieeexplore.ieee.org/iel7/97/4358004/09317747.pdf.
Jing Zhu et a., "EEG based depression recognition using improved graph convolutional neural network," Computers in Biology and Medicine, Jul. 2022, vol. 148, Elsevier, https://www.sciencedirect.com/science/article/abs/pii/S0010482522005765.

* cited by examiner

METHOD AND SYSTEM FOR EEG MOTOR IMAGERY CLASSIFICATION

PRIORITY CLAIM

This U.S. patent application claims priority under 35 U.S.C. § 119 to: Indian Patent Application No. 202221053592, filed on Sep. 19, 2022. The entire contents of the aforementioned application are incorporated herein by reference.

TECHNICAL FIELD

The disclosure herein generally relates to the field of Electroencephalogram (EEG) classification, and, more particularly, to method and system for EEG motor imagery classification.

BACKGROUND

Brain-computer interface (BCI) research has vast medical applications such as stroke rehabilitation and neural prosthesis. The BCI systems decode the patterns in brain activity to control electro-mechanical devices. One such BCI system is Electroencephalogram (EEG) based Motor Imagery. EEG is a popular method to record the brain's electrical activity due to its high temporal resolution and portability. Motor imagery (MI) can be defined as a subject's mental process of motor activity without actual movement. During the process of motor movement or imagery, the underlying functional connectivity within the sensory motor cortex changes resulting in an amplitude suppression or Event Related Desynchronization (ERD) or an amplitude increase or Event Related Synchronization (ERS) of central mu (8-12 Hz) and beta (18-25 Hz) rhythms. It is widely accepted that the process of MI involves similar cortical regions involved in the preparation or planning of movements. Hence, the motor imagery and movement preparation can be theorized as similar functional activities. Accurate classification of the neural activity is of great importance to enable these EEG based MI systems.

Spatio-temporal analysis of networks between lobes of the brain helps in learning about patterns of neuronal activity associated with motor functions. The most intuitive way to represent and analyze these networks is using graph which is a topographical representation consisting of a set of nodes and edges. In graph-based studies, typically, the nodes are defined in two ways: the first approach is to use source-space (EEG signal source i.e., the brain) to determine the nodes, usually captured from brain source imaging techniques or source reconstruction using EEG. Here, anatomical regions of the brain are used to generate the cortical networks or connectomes. The second method uses the sensor-space (EEG electrode position e.g., 10-20 electrode system) of the EEG acquisition systems to define the nodes. The EEG signals acquired at sensor level are described as a linear combination of the active brain and non-brain electrical sources whose activities are volume conducted on the scalp. Due to the volume conduction, many correlations exist between electrodes thereby reducing the spatial resolution which affect the detection of various functional interactions between brain regions. Existing deep learning works employ the sensor-space for EEG graph representations wherein the channels of the EEG are considered as nodes and connection between the nodes are either predefined or are based on certain heuristics. However, these representations are ineffective and fail to accurately capture the underlying brain's functional networks.

One recent work EEG-GAT: Graph Attention Networks for Classification of Electroencephalogram (EEG) Signals by Andac Demir et. al. discloses a method of generating EEG representations using a graph shift operator to learn the optimal connectivity pattern between EEG channels. But this method does not learn the importance of each edge (i.e., the edge weight). Also, the graph embedding or representation is obtained using the readout functions such as sum or mean which are static functions and may not accurately represent the graph. Another recent work EEG-GNN: Graph Neural Networks for Classification of Electroencephalogram (EEG) Signals by Andac Demir et. al. represents EEG signal as a graph, where nodes represent the EEG channels and the node connectivity (edges) is based on the policy formulated by neuro-scientist (for example, based on distance between electrodes). So, the accuracy of graph representation largely depends on expertise of the neuro-scientist.

SUMMARY

Embodiments of the present disclosure present technological improvements as solutions to one or more of the above-mentioned technical problems recognized by the inventors in conventional systems. For example, in one embodiment, a method for EEG motor imagery classification is provided. The method includes receiving one or more Electroencephalogram (EEG) signals and corresponding ground truth labels comprising a ground truth graph label, a ground truth edge label, and a ground truth node label. Each of the one or more EEG signals comprise a plurality of channels. The method further includes extracting a plurality of temporal embeddings corresponding to each of the plurality of channels of each of the one or more EEG signals using a temporal feature extractor. Further, the method includes constructing one or more graphs corresponding to each of the one or more EEG signals. Each of the one or more graphs comprise a plurality of nodes corresponding to the plurality of channels and a weighted adjacency matrix defining connectivity between each pair of nodes among the plurality of nodes. Each of the plurality of nodes is associated with the plurality of temporal embeddings of the corresponding channel. Furthermore, the method includes iteratively training a Graph Neural Network (GNN), the weighted adjacency matrix, a graph classifier, a node classifier, and an edge classifier for a plurality of pre-defined number of iterations by generating a plurality of node embeddings corresponding to each of the one or more EEG signals by the Graph Neural Network (GNN) using the one or more graphs; classifying each of the one or more EEG signals based on the corresponding plurality of node embeddings using the graph classifier, the node classifier, and the edge classifier to obtain a graph label, a node label and an edge label, wherein the graph label provides motor imagery classification, the node label provides quality of the EEG signal, and the edge label determines affinity between a pair of nodes among the plurality of nodes; and updating the GNN, the weighted adjacency matrix, the graph classifier, the node classifier, and the edge classifier based on a total loss obtained as a sum of a graph classification loss, a node classification loss, and an edge classification loss.

In another aspect, a system for EEG motor imagery classification is provided. The system includes a memory storing instructions; one or more communication interfaces; and one or more hardware processors coupled to the memory via the one or more communication interfaces, wherein the one or more hardware processors are configured by the instructions to: receive one or more Electroencephalogram (EEG) signals and corresponding ground truth labels comprising a ground truth graph label, a ground truth edge label, and a ground truth node label. Each of the one or more EEG signals comprise a plurality of channels. The one or more hardware processors are further configured to extract a plurality of temporal embeddings corresponding to each of the plurality of channels of each of the one or more EEG signals using a temporal feature extractor. Further, the one or more hardware processors are configured to construct one or more graphs corresponding to each of the one or more EEG signals. Each of the one or more graphs comprise a plurality of nodes corresponding to the plurality of channels and a weighted adjacency matrix defining connectivity between each pair of nodes among the plurality of nodes. Each of the plurality of nodes is associated with the plurality of temporal embeddings of the corresponding channel. Furthermore, the one or more hardware processors are configured to iteratively train a Graph Neural Network (GNN), the weighted adjacency matrix, a graph classifier, a node classifier, and an edge classifier for a plurality of pre-defined number of iterations by generating a plurality of node embeddings corresponding to each of the one or more EEG signals by the Graph Neural Network (GNN) using the one or more graphs; classifying each of the one or more EEG signals based on the corresponding plurality of node embeddings using the graph classifier, the node classifier, and the edge classifier to obtain a graph label, a node label and an edge label, wherein the graph label provides motor imagery classification, the node label provides quality of the EEG signal, and the edge label determines affinity between a pair of nodes among the plurality of nodes; and updating the GNN, the weighted adjacency matrix, the graph classifier, the node classifier, and the edge classifier based on a total loss obtained as a sum of a graph classification loss, a node classification loss, and an edge classification loss.

In yet another aspect, there are provided one or more non-transitory machine-readable information storage mediums comprising one or more instructions which when executed by one or more hardware processors cause a method for EEG motor imagery classification. The method includes receiving one or more Electroencephalogram (EEG) signals and corresponding ground truth labels comprising a ground truth graph label, a ground truth edge label, and a ground truth node label. Each of the one or more EEG signals comprise a plurality of channels. The method further includes extracting a plurality of temporal embeddings corresponding to each of the plurality of channels of each of the one or more EEG signals using a temporal feature extractor. Further, the method includes constructing one or more graphs corresponding to each of the one or more EEG signals. Each of the one or more graphs comprise a plurality of nodes corresponding to the plurality of channels and a weighted adjacency matrix defining connectivity between each pair of nodes among the plurality of nodes. Each of the plurality of nodes is associated with the plurality of temporal embeddings of the corresponding channel. Furthermore, the method includes iteratively training a Graph Neural Network (GNN), the weighted adjacency matrix, a graph classifier, a node classifier, and an edge classifier for a plurality of pre-defined number of iterations by generating a plurality of node embeddings corresponding to each of the one or more EEG signals by the Graph Neural Network (GNN) using the one or more graphs; classifying each of the one or more EEG signals based on the corresponding plurality of node embeddings using the graph classifier, the node classifier, and the edge classifier to obtain a graph label, a node label and an edge label, wherein the graph label provides motor imagery classification, the node label provides quality of the EEG signal, and the edge label determines affinity between a pair of nodes among the plurality of nodes; and updating the GNN, the weighted adjacency matrix, the graph classifier, the node classifier, and the edge classifier based on a total loss obtained as a sum of a graph classification loss, a node classification loss, and an edge classification loss.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Existing EEG based MI classification methods construct graphs using static adjacency matrix that are either predefined or based on certain heuristics. Hence, the constructed graph does not accurately represent the EEG signal. Embodiments of present disclosure generates a representation (embedding) of the EEG signal by feeding a graph as input to a trained Graph Neural Network (GNN). The graph comprises nodes corresponding to EEG channels and connectivity between the nodes is defined by a weighted adjacency matrix. The GNN and weighted adjacency matrix are trained together using training samples unlike state of the art methods. Thus, the embedding generated by the trained GNN accurately represents the EEG signal and therefore can be used for accurate motor imagery classification (i.e. graph classification). In addition, the embedding can also be used for node and edge classification by using appropriate classifiers.

Figure 1:
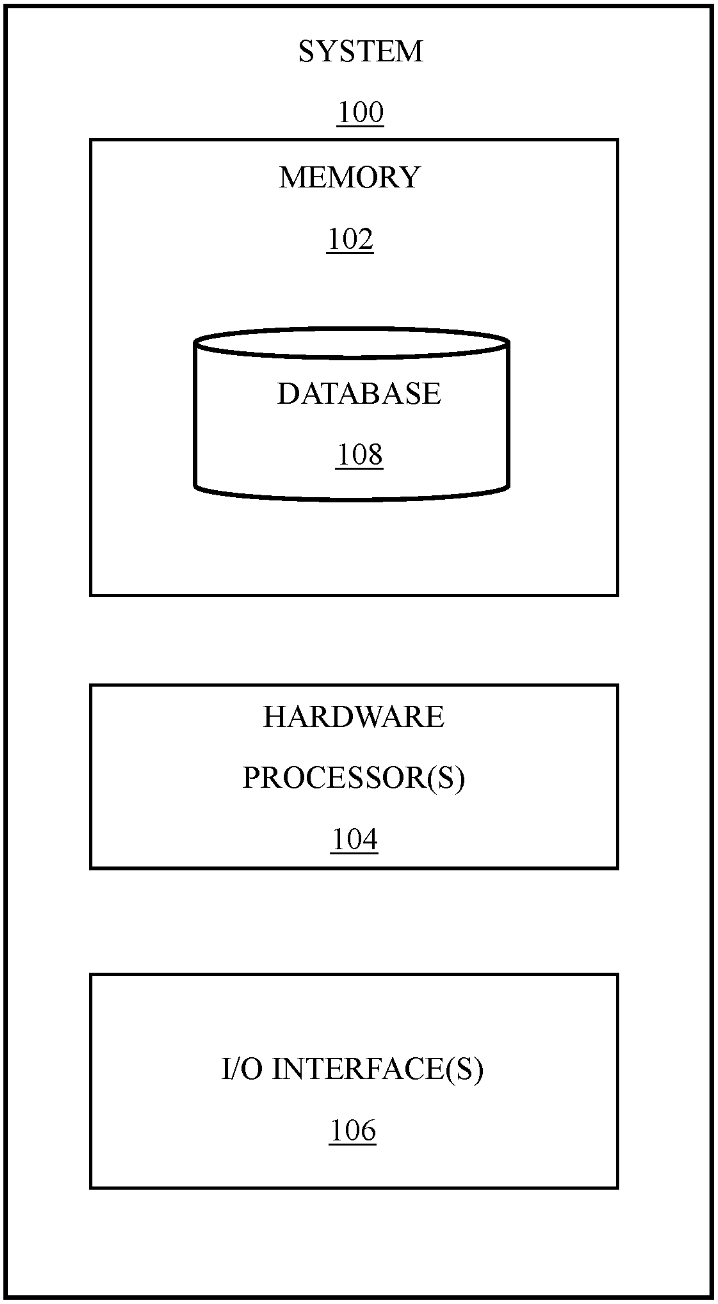
FIG. 1 illustrates an exemplary block diagram of a system for EEG motor imagery classification, according to some embodiments of the present disclosure.
Figure 2A:
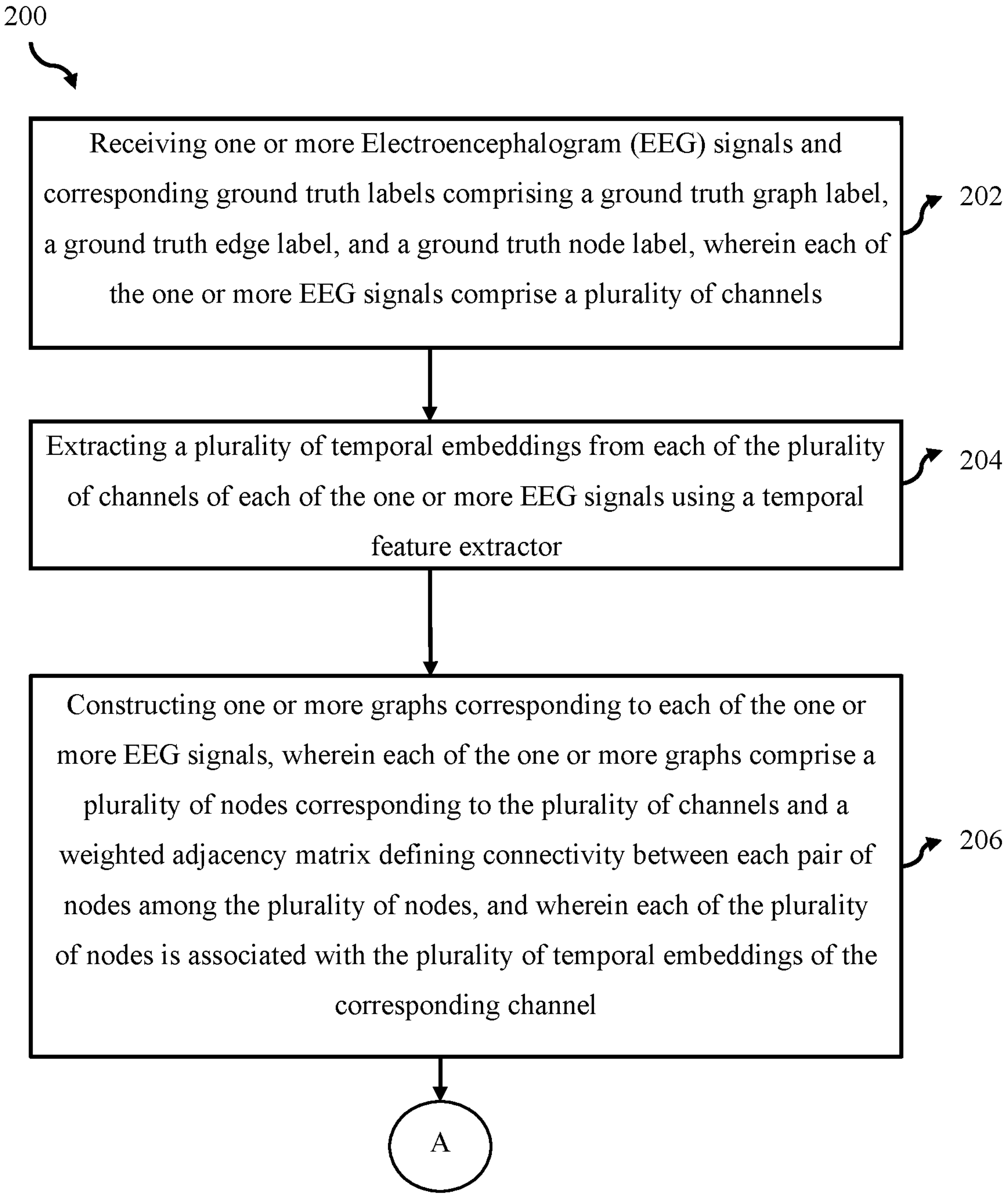
FIGS. 2A and 2B collectively referred as FIG. 2 is a flow diagram illustrating method for training a model comprising a Graph Neural Network and classifiers for EEG signal classification, according to some embodiments of the present disclosure.
Figure 2B:
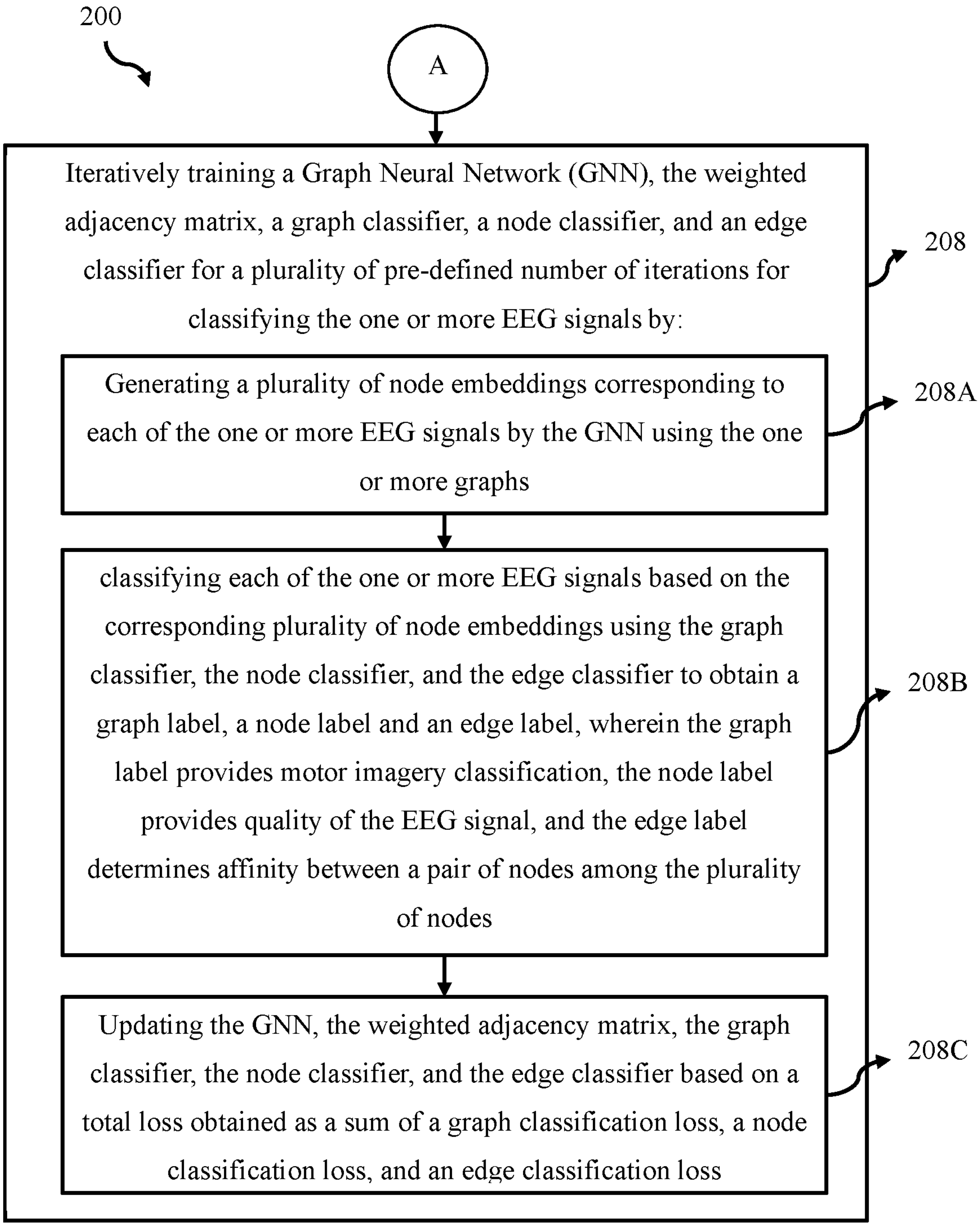
Figure 3:
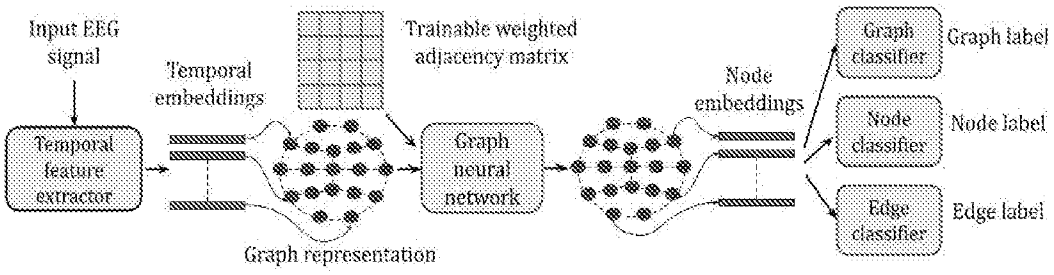
FIG. 3 is a functional block diagram illustrating method of EEG motor imagery classification, according to some embodiments of the present disclosure.

Referring now to the drawings, and more particularly to FIG. 1 through 3, where similar reference characters denote corresponding features consistently throughout the figures, there are shown preferred embodiments and these embodiments are described in the context of the following exemplary system and/or method.

FIG. 1 illustrates an exemplary block diagram of a system for EEG motor imagery classification. In an embodiment, the system 100 includes one or more processors 104, communication interface device(s) 106 or Input/Output (I/O) interface(s) 106 or user interface 106, and one or more data storage devices or memory 102 operatively coupled to the one or more processors 104. The memory 102 comprises a database 108. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud, and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) 106 receives an EEG signal as input and gives classification of the EEG signal as output. The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. Functions of the components of system 100 are explained in conjunction with flow diagrams depicted in FIGS. 2 and 3 for EEG motor imagery classification.

In an embodiment, the system 100 comprises one or more data storage devices or the memory 102 operatively coupled to the processor(s) 104 and is configured to store instructions for execution of steps of the method (200) depicted in FIG. 2 by the processor(s) or one or more hardware processors 104. The steps of the method of the present disclosure will now be explained with reference to the components or blocks of the system 100 as depicted in FIG. 1, the steps of flow diagram as depicted in FIGS. 2 and 3. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

FIG. 2 is a flow diagram illustrating method for training a model comprising a Graph Neural Network and classifiers for EEG signal classification, according to some embodiments of the present disclosure. The steps of method 200 are explained in conjunction with functional block diagram illustrated in FIG. 3. At step 202 of the method 200, the one or more hardware processors 104 are configured to receive one or more EEG signals and their corresponding ground truth labels comprising ground truth graph label, ground truth node label and ground truth edge label. Each of the one or more EEG signals comprise a plurality of channels which are electrodes capturing brainwave activity. For example, an EEG signal recorded by a 16-electrode EEG device has 16 channels.

Once the one or more EEG signals are received, at step 204 of the method 200 the one or more hardware processors are configured to extract a plurality of temporal embeddings (alternatively referred as temporal features) from each of the plurality of channels of each of the one or more EEG signals via a temporal feature extractor illustrated in FIG. 3. The temporal feature extractor is a neural network such as Recurrent Neural Network (RNN), temporal convolutional neural network, transformer etc. An example architecture of the temporal feature extractor is given in table 1 where N represents number of channels in the one or more EEG signals and T represents the duration of the one or more EEG signals which is expressed in terms of number of samples. For example, an EEG signal of 3 seconds sampled at the rate of 100 samples/sec will yield 300 samples, therefore T=300. The 1D convolution layers (Conv1D) and the average pooling layers (Avg. pool) extract the plurality of temporal features $h^0$ of each channel of each of the one or more EEG signals. The output of the temporal feature extractor is given by equation 1, wherein x represents the one or more EEG signals with N channels, f represents the temporal feature extractor with parameters $\theta_f$, and $h^0$ represents the plurality of temporal embeddings corresponding to the one or more EEG signals. The temporal embeddings indicate activity and nature of the EEG signals, for example, entropy, coherence etc.

$$h^0 = f(x, \theta_f) \tag{1}$$

TABLE 1

| Layer | Kernel | Stride | Padding | Input | Output |
|---|---|---|---|---|---|
| Conv1D | 15 | 1 | same | N, T | N, T |
| Avg. pool | 2 | 2 | valid | N, T | N, T/2 |
| Conv1D | 15 | 1 | same | N, T/2 | N, T/2 |
| Avg. pool | 2 | 2 | valid | N, T/2 | N, T/4 |

Once the temporal features are extracted, one or more graphs (G) are constructed corresponding to each of the one or more EEG signals at step 206 of the method 200. Each graph comprises a plurality of nodes corresponding to each of the plurality of channels of corresponding EEG signal among the one or more EEG signals and a weighted adjacency matrix ($A_W$) defining connectivity (alternatively referred as edges) between each pair of nodes among the plurality of nodes. Each of the plurality of nodes is associated with the plurality of temporal embeddings ($h^0$) of the corresponding channel.

Once the one or more graphs are constructed, at step 208 of the method 500, the one or more hardware processors are configured to iteratively train a Graph Neural Network (GNN), the weighted adjacency matrix, a graph classifier, a node classifier, and an edge classifier for a plurality of pre-defined number of iterations by steps 208A to 208C. At step 208A, a plurality of node embeddings ($h^n$) corresponding to each of the one or more EEG signals are generated by the GNN using the one or more graphs according to equation 2. As understood by a person skilled in the art, each node embedding is a feature vector that represents each node in each of the one or more graphs. Thus, the plurality of node embeddings together represent the entire graph and the corresponding EEG signal. In the first iteration of training, the temporal embeddings associated with the nodes of the one or more graphs are considered as $h^{old}$ in equation 2. In the subsequent iterations, the node embeddings generated at the previous iteration are considered as $h^{old}$. $h^{new}$ represents updated node embedding generated by the GNN at a current iteration. In general, $i^{th}$ node embedding is given by equation 3, wherein $\mathcal{N}_i$ represents set of nodes that are in neighborhood of node i in the one or more graphs, W represents a transformation matrix which is used to transform the $h^{old}$ to $h^{new}$ and can be updated during training of the GNN, b represents bias, and $\sigma$ represents non-linearity (for example, ReLu). The node embedding generated at the end of the plurality of iterations is given by equation 4, wherein $h^0$ is the temporal embedding, $A_W$ is the weighted adjacency matrix and $\theta_{GNN}$ is weights of the GNN.

$$h^{new} = GNN(h^{old}, A_W{:}\theta_{GNN}) \tag{2}$$

$$h_i^{new} = \sigma\left(\sum_{j \in N_i} A_{j,i} h_j^{old} W + b\right) \tag{3}$$

$$h^n = GNN(h^0, A_W; \theta_{GNN}) \tag{4}$$

Once the node embeddings are generated, each of the one or more EEG signals are classified, at the step 208B, based on the corresponding plurality of node embeddings using the graph classifier, the node classifier, and the edge classifier to obtain a graph label, a node label, and an edge label. The graph label provides motor imagery classification, the node label provides quality of the EEG signal (for example, good or poor), and the edge label determines affinity between a pair of nodes among the plurality of nodes (for example, strong or weak). In an embodiment, the node embeddings are vectorized or flattened before feeding into the graph classifier. Similarly, the node embeddings are concatenated before feeding into the edge classifier while they are fed as it is into the node classifier to classify the one or more EEG signals. Example architectures of the graph classifier, the node classifier and the edge classifier are given in tables 2, 3 and 4, respectively. Here, N represents number of channels in the one or more EEG signals, T represents length of the one or more EEG signals expressed in terms of samples, $h_{in}$ and $h_{out}$ represent the number of input and output neurons of the fully connected (FC) layer, $\mathcal{C}_{nodes}$ is number of node categories and $\mathcal{C}_{edge}$ is number of edge categories.

TABLE 2

| Layer | $h_{in}$ | $h_{out}$ | input | output |
|---|---|---|---|---|
| Flatten | — | — | N, T/4 | N × T/4 |
| FC | N × T/4 | 64 | N × T/4 | 64 |
| FC | 64 | 4 or 2 | 64 | 4 or 2 |

TABLE 3

| Layer | $h_{in}$ | $h_{out}$ | input | output |
|---|---|---|---|---|
| FC | T/4 | 64 | T/4 | 64 |
| FC | 64 | $\mathcal{C}_{nodes}$ | 64 | $\mathcal{C}_{nodes}$ |

TABLE 4

| Layer | $h_{in}$ | $h_{out}$ | input | output |
|---|---|---|---|---|
| Concat | — | — | [T/4], [T/4] | T/2 |
| FC | T/2 | 64 | T/2 | 64 |
| FC | 64 | $\mathcal{C}_{edges}$ | 64 | $\mathcal{C}_{edges}$ |

The graph label $\hat{y}^{graph}$ is predicted according to equation 5, wherein h is vectorized node embedding, $\theta_{graph}$ represents parameters of the graph classifier and $Cls_{graph}$ represents the graph classifier. Once the graph label is predicted, a graph classification loss is calculated based on the predicted graph label and the ground truth graph label. An example calculation is given by equation 6, wherein CE is cross entropy loss which calculates additional values required to predict ground truth $y^{graph}$ instead of the predicted classification $\hat{y}^{graph}$. As understood by a person skilled in the art, other loss functions such as variants of cross entropy loss, hinge loss, supervised contrastive loss etc. can be used instead in alternate embodiments. The node label $\hat{y}^{node}$ for $i^{th}$ node in a graph among the one or more graphs is predicted according to equation 7, wherein $h_i$ is the node embedding of the $i^{th}$ node, $Cls_{node}$ represents the node classifier, and $\theta_{node}$ represents parameters of the node classifier. Once the node label is predicted, a node classification loss is calculated based on the predicted node label and ground truth node label. An example calculation is given by equation 8, wherein N is total number of nodes in a graph among the one or more graphs, CE is cross entropy loss which calculates additional values required to predict ground truth $y^{node}$ instead of the predicted classification $\hat{y}^{node}$. The edge label $\hat{y}^{edge}$ for an edge connecting a node i and a node j in a graph among the one or more graphs is predicted according to equation 9, wherein $h_i$ and $h_j$ are the node embeddings of the node i and node j respectively, $Cls_{edge}$ represents the edge classifier, and $\theta_{edge}$ represents the parameter of the edge classifier. All the edges in the graph can be classified in a similar way to obtain the edge labels. Once the edges are classified, an edge classification loss is calculated based on predicted edge label and ground truth edge label. An example calculation is given in equation 10, wherein |E| is total number of edges in a graph among the one or more graphs, CE is cross entropy loss which calculates additional values required to predict ground truth $y_{i,j}^{edge}$ instead of the predicted classification $\hat{y}_{i,j}^{edge}$ for the edge $e_{i,j}$ connecting node i and node j.

$$\hat{y}^{graph} = Cls_{graph}(h; \theta_{graph}) \tag{5}$$

$$\mathcal{L}_{graph} = CE(\hat{y}^{graph}, y^{graph}) \tag{6}$$

$$\hat{y}^{node} = Cls_{node}(h_i; \theta_{node}) \tag{7}$$

$$\mathcal{L}_{node} = \frac{1}{N}\sum_{i=1}^{N} CE(\hat{y}^{node}, y^{node}) \tag{8}$$

$$\hat{y}^{edge} = Cls_{edge}(h_i, h_j; \theta_{edge}) \tag{9}$$

$$\mathcal{L}_{edge} = \frac{1}{|E|}\sum_{e_{i,j} \in E} CE(\hat{y}_{i,j}^{edge}, y_{i,j}^{edge}) \tag{10}$$

Once the one or more EEG signals are classified and classification losses are calculated, a total loss is determined as sum of graph classification loss, node classification loss and the edge classification loss according to equation 11. Further, the GNN, the weighted adjacency matrix, the graph classifier, the node classifier, and the edge classifier are updated based on the total loss at the step 208C. Unlike state of the art methods where the weighted adjacency matrix is pre-defined or based on certain heuristics, in the method of present disclosure, it is learnt along with the GNN to accurately represent the EEG signals.

$$\mathcal{L}_{total} = \mathcal{L}_{graph} + \mathcal{L}_{node} + \mathcal{L}_{edge} \tag{11}$$

For updating the GNN, the weighted adjacency matrix, the graph classifier, the node classifier, and the edge classifier a first, a second, a third, a fourth and a fifth gradient of the total loss with respect to parameters of the GNN, the weighted adjacency matrix, the graph classifier, the node classifier, and the edge classifier, respectively are calculated. Then, the GNN, the weighted adjacency matrix, the graph classifier, the node classifier, and the edge classifier are updated using an optimizer (for example, Adam optimizer) based on the computed first, second, third, fourth and fifth gradient.

Once the GNN, the weighted adjacency matrix and the classifiers are trained by the step 208, they can be used for classifying any input EEG signal as illustrated in FIG. 3. Initially, an input EEG signal comprising a plurality of channels is received and temporal embedding of each of the plurality of channels is extracted using the temporal feature extractor. Further, a graph is constructed with the plurality of channels as nodes and the trained weighted adjacency matrix defines the edges between the nodes. Each node is associated with the temporal embedding of the corresponding channel. Further, node embeddings are generated by the trained GNN for each node of the graph which are fed into the trained graph classifier, the node classifier, and the edge classifier to classify the EEG signal. Since the EEG signal is accurately represented by the weighted adjacency matrix, the classifications are also accurate. Also, the method of present disclosure is able to determine graph label, node label, and edge label using same node embeddings generated by the GNN unlike state of the art methods which provide only graph classification. Thus, the method of present disclosure is more accurate and has a wider range of applications than the state of the art methods.

Experimental Results

The experimental results are provided to highlight effectiveness of the method of present disclosure on the EEG MI classification task (i.e. graph classification). Pytorch with Deep Graph Library (DGL) is used for the experiments. The term 'model' is used to together refer to the GNN, temporal feature extractor, and the graph classifier.

Dataset: The dataset used is physionet EEG motor movement and imagery dataset (EEG-MMIDB) (G. Schalk et. al., "Bci2000: a general-purpose brain-computer interface (bci) system," IEEE Transactions on biomedical engineering, vol. 51, no. 6, pp. 1034-1043, 2004; A. L. Goldberger et. al., "Physiobank, physiotoolkit, and physionet: components of a new research resource for complex physiologic signals," circulation, vol. 101, no. 23, pp. e215-e220, 2000). The dataset contains EEG signals recorded from 109 subjects. The EEG signals were obtained via BCI2000 system using 64-channels at a sampling rate of 160 Hz. Each subject participated in 3 trials of left, right, both fists and both feet motor imagery and movement. The EEG signals are preprocessed by performing average re-referencing and z-scoring before performing the method of present disclosure and no other artifact removal techniques were used.

Following are the details of the dataset used for experiments: (i) Two class subset: For the two-class classification task, EEG signals of subjects performing the following activities are considered—(a) imagine open and close of left fist, and (b) imagine open and close of right fist; (ii) Four class subset: For the four-class classification task, EEG signals of subjects performing the following activities are considered—(a) imagine open and close of left fist, (b) imagine open and close of right fist, (c) imagine open and close of both feet; and (d) resting. Two versions of the EEG trial data are taken for training and testing of the models. They are: (i) 6 seconds duration: The duration of each EEG trial is 6 seconds. The trial data consists of 4 seconds of imagery activity, and 1 second of resting-state before and after the start of imagery activity; (ii) 3 seconds duration: The duration of each EEG trial is 3 seconds. The trial data consists of first 3 seconds of imagery activity.

Evaluation: the performance of the proposed method is evaluated in a cross-subject setting wherein the model is evaluated on the EEG signals from the subjects that are not part of the training set, i.e., disjoint sets of subjects are used for training and testing. The mean accuracy of the model for 5-fold cross-validation is reported and compared with the following methods: (i) Park et al. ("Augmented complex common spatial patterns for classification of noncircular eeg from motor imagery tasks," IEEE Transactions on neural systems and rehabilitation engineering, vol. 22, no. 1, pp. 1-10, 2013): The method uses a complex-valued, common spatial pattern (CSP) algorithm with the Strong Uncorrelating Transform (SUT) for feature extraction. A Support Vector Machine (SVM) is trained on the extracted features for the motor imagery classification task; (ii) Dose et al. ("A deep learning mi-eeg classification model for bcis." in EUSIPCO, 2018, pp. 1676-1679): This method represents EEG signals as a 2D grid, where each row represents the signal of a particular EEG lead. 2D convolution layers are used to extract the Spatio-temporal features. These features are fed to a fully connected layer to obtain the final prediction. This method considers raw EEG signals for feature extraction. The experimental setup and evaluation protocol used to evaluate method of present disclosure are similar to the Dose et al.

Results: Table 5 shows the performance of the models on the two-class dataset. The accuracy of the model in the subject independent setting is shown. The method of present disclosure achieves a mean accuracy of 82.92%. Further, it can be observed that the performance of the method of present disclosure is better than the existing approaches. Table 6 shows the performance of the models on the four-class dataset. The models are trained and tested on EEG signals with different durations. The method of present disclosure achieves a mean accuracy of 64.38% and 68.60% on the cross-validation set containing EEG signals with a duration of 3 and 6 seconds, respectively.

TABLE 5

| Methods | Number of channels | Accuracy (%) |
|---|---|---|
| Park et. al. | 58 | 72.37 |
| Dose et. al. | 64 | 80.10 |
| Method of present disclosure | 64 | 82.92 |

TABLE 6

| Method | Duration | Accuracy(%) |
|---|---|---|
| Dose et. al. | 3 | 59.71 |
| | 6 | 65.73 |
| Method of present | 3 | 64.38 |
| disclosure | 6 | 68.60 |

Ablation study: Following ablation experiments are performed to highlight the effectiveness of the method of present disclosure. (i) Ablation-1: Temporal convolution and GNN with a fixed adjacency matrix. In this experiment, the temporal feature for each channel is obtained by the temporal convolution block. Then the GNN with a fixed adjacency matrix is used to aggregate channel features. This experiment is performed to highlight the need for GNN with a trainable adjacency matrix. Table 7 shows the result for this experiment. It can be observed that there is a drop in the performance of the model from 68.60% to 59.22%. (ii) Ablation-2: Temporal convolution with pooling-based channel feature aggregation. In this experiment, the temporal features of each channel are obtained by the temporal convolution block. Instead of GNN, a pooling layer (such as mean, sum, and max) is used to aggregate the channel features. This experiment is performed to highlight the importance of the GNN with a trainable weighted adjacency matrix. Table 7 shows the result for this experiment. It can be observed that there is a drop in the performance of the model from 68.60% to 56.97%, 57.86%, and 57.71% for mean, max, and sum pooling layers, respectively.

TABLE 7

| Method | Duration (seconds) | Accuracy(%) |
|---|---|---|
| Ablation-1 | 6 | 59.22 |
| | Ablation-2 | |
| Mean pool | 6 | 56.97 |
| Max pool | 6 | 57.86 |
| Sum pool | 6 | 57.71 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method comprising:

receiving, via one or more hardware processors, one or more Electroencephalogram (EEG) signals and corresponding ground truth labels comprising a ground truth graph label, a ground truth edge label, and a ground truth node label, wherein each of the one or more EEG signals comprise a plurality of channels;

extracting, via the one or more hardware processors, a plurality of temporal embeddings corresponding to each of the plurality of channels of each of the one or more EEG signals using a temporal feature extractor;

constructing, via the one or more hardware processors, one or more graphs corresponding to each of the one or more EEG signals, wherein each of the one or more graphs comprise a plurality of nodes corresponding to the plurality of channels and a weighted adjacency matrix defining connectivity between each pair of nodes among the plurality of nodes, and wherein each of the plurality of nodes is associated with the plurality of temporal embeddings of the corresponding channel; and iteratively training, via the one or more hardware processors, a Graph Neural Network (GNN), the weighted adjacency matrix, a graph classifier, a node classifier, and an edge classifier for a plurality of pre-defined number of iterations for classifying the one or more EEG signals by:

generating a plurality of node embeddings corresponding to each of the one or more EEG signals by the GNN using the one or more graphs;

classifying each of the one or more EEG signals based on the corresponding plurality of node embeddings using the graph classifier, the node classifier, and the edge classifier to obtain a graph label, a node label, and an edge label, wherein the graph label provides motor imagery classification, the node label provides quality of the EEG signal, and the edge label determines affinity between a pair of nodes among the plurality of nodes; and updating the GNN, the weighted adjacency matrix, the graph classifier, the node classifier, and the edge classifier based on a total loss obtained as a sum of a graph classification loss, a node classification loss, and an edge classification loss, wherein the GNN, the weighted adjacency matrix, the graph classifier, the node classifier, and the edge classifier are updated by:

calculating a first, a second, a third, a fourth and a fifth gradient of the total loss with respect to parameters of the GNN, the weighted adjacency matrix, the graph classifier, the node classifier, and the edge classifier; and updating the GNN, the weighted adjacency matrix, the graph classifier, the node classifier, and the edge classifier using an optimizer based on the computed first, second, third, fourth and fifth gradient.

2. The method of claim 1, wherein the GNN, the graph classifier, the node classifier, and the edge classifier are used to classify a test EEG signal during inference based on a graph constructed using the weighted adjacency matrix and a plurality of temporal embeddings corresponding to each of a plurality of channels of the test EEG signal.

3. The method of claim 1, wherein the plurality of node embeddings are vectorized before feeding into the graph classifier.

4. The method of claim 1, wherein the plurality of node embeddings are concatenated before feeding into the edge classifier.

5. A system comprising:

a memory storing instructions;

one or more communication interfaces; and one or more hardware processors coupled to the memory via the one or more communication interfaces, wherein the one or more hardware processors are configured by the instructions to:

receive one or more Electroencephalogram (EEG) signals and corresponding ground truth labels comprising a ground truth graph label, a ground truth edge label, and a ground truth node label, wherein each of the one or more EEG signals comprise a plurality of channels;

extract a plurality of temporal embeddings corresponding to each of the plurality of channels of each of the one or more EEG signals using a temporal feature extractor;

construct one or more graphs corresponding to each of the one or more EEG signals, wherein each of the one or more graphs comprise a plurality of nodes corresponding to the plurality of channels and a weighted adjacency matrix defining connectivity between each pair of nodes among the plurality of nodes, and wherein each of the plurality of nodes is associated with the plurality of temporal embeddings of the corresponding channel; and iteratively train a Graph Neural Network (GNN), the weighted adjacency matrix, a graph classifier, a node classifier, and an edge classifier for a plurality of pre-defined number of iterations for classifying the one or more EEG signals by:

generating a plurality of node embeddings corresponding to each of the one or more EEG signals by the GNN using the one or more graphs;

classifying each of the one or more EEG signals based on the corresponding plurality of node embeddings using the graph classifier, the node classifier, and the edge classifier to obtain a graph label, a node label, and an edge label, wherein the graph label provides motor imagery classification, the node label provides quality of the EEG signal, and the edge label determines affinity between a pair of nodes among the plurality of nodes; and updating the GNN, the weighted adjacency matrix, the graph classifier, the node classifier, and the edge classifier based on a total loss obtained as a sum of a graph classification loss, a node classification loss, and an edge classification loss, wherein one or more hardware processors are configured to update the GNN, the weighted adjacency matrix, the graph classifier, the node classifier, and the edge classifier by:

calculating a first, a second, a third, a fourth and a fifth gradient of the total loss with respect to parameters of the GNN, the weighted adjacency matrix, the graph classifier, the node classifier, and the edge classifier; and updating the GNN, the weighted adjacency matrix, the graph classifier, the node classifier, and the edge classifier using an optimizer based on the computed first, second, third, fourth and fifth gradient.

6. The system of claim 5, wherein the GNN, the graph classifier, the node classifier, and the edge classifier are used to classify a test EEG signal during inference based on a graph constructed using the weighted adjacency matrix and a plurality of temporal embeddings corresponding to each of a plurality of channels of the test EEG signal.

7. The system of claim 5, wherein the one or more hardware processors are configured to vectorize the plurality of node embeddings before feeding into the graph classifier.

8. The system of claim 5, wherein the one or more hardware processors are configured to concatenate the plurality of node embeddings before feeding into the edge classifier.

9. One or more non-transitory machine-readable information storage mediums comprising one or more instructions which when executed by one or more hardware processors cause:

receiving one or more Electroencephalogram (EEG) signals and corresponding ground truth labels comprising a ground truth graph label, a ground truth edge label, and a ground truth node label, wherein each of the one or more EEG signals comprise a plurality of channels;

extracting a plurality of temporal embeddings corresponding to each of the plurality of channels of each of the one or more EEG signals using a temporal feature extractor;

constructing one or more graphs corresponding to each of the one or more EEG signals, wherein each of the one or more graphs comprise a plurality of nodes corresponding to the plurality of channels and a weighted adjacency matrix defining connectivity between each pair of nodes among the plurality of nodes, and wherein each of the plurality of nodes is associated with the plurality of temporal embeddings of the corresponding channel; and iteratively training a Graph Neural Network (GNN), the weighted adjacency matrix, a graph classifier, a node classifier, and an edge classifier for a plurality of pre-defined number of iterations for classifying the one or more EEG signals by:

generating a plurality of node embeddings corresponding to each of the one or more EEG signals by the GNN using the one or more graphs;

classifying each of the one or more EEG signals based on the corresponding plurality of node embeddings using the graph classifier, the node classifier, and the edge classifier to obtain a graph label, a node label, and an edge label, wherein the graph label provides motor imagery classification, the node label provides quality of the EEG signal, and the edge label determines affinity between a pair of nodes among the plurality of nodes; and updating the GNN, the weighted adjacency matrix, the graph classifier, the node classifier, and the edge classifier based on a total loss obtained as a sum of a graph classification loss, a node classification loss, and an edge classification loss, wherein the GNN, the weighted adjacency matrix, the graph classifier, the node classifier, and the edge classifier are updated by:

calculating a first, a second, a third, a fourth and a fifth gradient of the total loss with respect to parameters of the GNN, the weighted adjacency matrix, the graph classifier, the node classifier, and the edge classifier; and updating the GNN, the weighted adjacency matrix, the graph classifier, the node classifier, and the edge classifier using an optimizer based on the computed first, second, third, fourth and fifth gradient.

10. The one or more non-transitory machine-readable information storage mediums of claim 9, wherein the GNN, the graph classifier, the node classifier, and the edge classifier are used to classify a test EEG signal during inference based on a graph constructed using the weighted adjacency matrix and a plurality of temporal embeddings corresponding to each of a plurality of channels of the test EEG signal.

11. The one or more non-transitory machine-readable information storage mediums of claim 9, wherein the plurality of node embeddings are vectorized before feeding into the graph classifier.

12. The one or more non-transitory machine-readable information storage mediums of claim 9, wherein the plurality of node embeddings are concatenated before feeding into the edge classifier.

* * * * *